United States Patent
Kawaguchi et al.

(10) Patent No.: US 10,502,703 B2
(45) Date of Patent: Dec. 10, 2019

(54) PERACETIC ACID CONCENTRATION METER

(71) Applicant: HORIBA Advanced Techno, Co., Ltd., Kyoto-shi, Kyoto (JP)

(72) Inventors: Yoshihiko Kawaguchi, Kyoto (JP); Satoko Kai, Kyoto (JP)

(73) Assignee: HORIBA Advanced Techno, Co., Ltd., Kyoto-shi, Kyoto (JP)

( * ) Notice: Subject to any disclaimer, the term of this patent is extended or adjusted under 35 U.S.C. 154(b) by 120 days.

(21) Appl. No.: 14/728,903

(22) Filed: Jun. 2, 2015

(65) Prior Publication Data

US 2015/0346139 A1    Dec. 3, 2015

(30) Foreign Application Priority Data

Jun. 3, 2014 (JP) .................. 2014-114878
Jun. 3, 2014 (JP) .................. 2014-114879

(51) Int. Cl.
*G01N 27/404* (2006.01)

(52) U.S. Cl.
CPC ....... *G01N 27/404* (2013.01); *G01N 27/4045* (2013.01)

(58) Field of Classification Search
CPC .. G01N 27/404; G01N 27/4045; G01N 27/40; G01N 27/49
See application file for complete search history.

(56) References Cited

U.S. PATENT DOCUMENTS

| 5,384,029 A | 1/1995 | Campbell |
| 5,770,039 A | 6/1998 | Rigney et al. |
| 2002/0005352 A1 | 1/2002 | Offenbacher |

FOREIGN PATENT DOCUMENTS

| DE | 4319002 A1 | 2/1995 |
| JP | 357014049 U1 | 1/1982 |
| JP | 360074043 U | 5/1985 |
| JP | 62076445 A | 4/1987 |
| JP | S63234146 A | 9/1988 |
| JP | H02057960 A | 2/1990 |
| JP | 04343065 A | 11/1992 |
| JP | H04-34306 5 A1 * | 11/1992 |
| JP | H05035823 B2 | 5/1993 |
| JP | 2001013102 A | 1/2001 |

(Continued)

OTHER PUBLICATIONS

English machine translation of JP 2011-080969, A (Year: 2011).*

(Continued)

*Primary Examiner* — J. Christopher Ball
(74) *Attorney, Agent, or Firm* — Alleman Hall Creasman & Tuttle LLP (57) ABSTRACT

A main object of the present invention is to provide a membrane covered type peracetic acid concentration meter that can prevent various common problems, including problems that occur in the event of an internal solution leak into a sample solution. The membrane covered type peracetic acid concentration meter adapted to measure the concentration of peracetic acid in the sample solution includes: a membrane that allows peracetic acid to permeate; and the internal solution that dissolves peracetic acid having permeated the membrane. In addition, as the internal solution, a buffer solution having a buffering action on hydrogen ion concentration is used.

8 Claims, 10 Drawing Sheets

(56) References Cited

FOREIGN PATENT DOCUMENTS

| | | | |
|---|---|---|---|
| JP | 2002195975 A | 7/2002 |
| JP | 2002530672 A | 9/2002 |
| JP | 2003202315 A | 7/2003 |
| JP | 2003294694 A | 10/2003 |
| JP | 2009122112 A | 6/2009 |
| JP | 2010060391 A | 3/2010 |
| JP | 2010243452 A | 10/2010 |
| JP | 2011080969 A | 4/2011 |

OTHER PUBLICATIONS

Japan Patent Office, Office Action Issued in Japanese Application No. 2014-114878, dated Jul. 13, 2017, 3 pages.
Japan Patent Office, Office Action Issued in Japanese Application No. 2014-114879, dated Jul. 13, 2017, 3 pages.
Japanese Patent Office, Office Action Issued in Application No. 2014114878, dated May 1, 2018, 6 pages.
State Intellectual Property Office of the People's Republic of China, Office Action and Search Report Issued in Application No. 201510297253.4, dated May 18, 2018, 11 pages.

\* cited by examiner

PERACETIC ACID CONCENTRATION METER

TECHNICAL FIELD

The present invention relates to a peracetic acid concentration meter adapted to measure the concentration of peracetic acid in a sample solution.

BACKGROUND ART

A peracetic acid solution is a solution commonly used for disinfection/sterilization in fields such as medicine, and food production. Peracetic acid is an unstable substance that decomposes with time. Consequently, significant changes in the concentration of peracetic acid in a solution can occur, making it necessary to monitor and control its concentration.

One example of a commonly used method for measuring peracetic acid concentration is described in Patent Literature 1. The method described in Patent Literature 1 teaches measuring the concentration of peracetic acid by measuring the amount of change in oxidation reduction potential in the reaction between peracetic acid, contained in a sample solution, and iodide ions, contained in an inter solution of a measuring device. When applying the method described above it is possible to substitute iodide ions with bromide ions.

A second commonly used acid concentration measuring method is described in Patent Literature 2, and involves the use of a membrane covered type sensor. The method described in Patent Literature 2 is primarily used for measuring concentration of hydrogen peroxide, but can also be applied to measuring the concentration of peracetic acid.

The membrane covered type sensor described in Patent Literature 2 includes: a hydrogen peroxide-permeable tubular body; rubber plugs that close up the opposite ends of the tubular body; electrodes (a working electrode and an counter electrode) held in the tubular body; an internal solution; and an enzyme fixing film disposed outside the tubular body.

The membrane covered type sensor described in Patent Literature 2 senses hydrogen peroxide by sensing the strength of an electric current that is generated when hydrogen peroxide in a sample solution comes in contact with the internal solution, and an oxidation-reduction reaction takes place at the electrode surface. Also, in the membrane covered type sensor described in Patent literature 2, silicon rubber superior in flexibility and elasticity is used for the hydrogen peroxide-permeable tubular body.

CITATION LIST

Patent Literature

Patent Literature 1: JP-A2003-294694
Patent Literature 1: JP-A04-343065

SUMMARY OF INVENTION

Technical Problem

In the case of applying the measuring method described in Patent Literature 1 to a membrane covered type peracetic acid concentration meter, a number of problems may arise. One potential problem is contamination of the sample by leakage of the inter solution of the concentration meter may due to breakage, defective adhesion, or the like, of a membrane. Such leaks are troublesome, since the inter solution contains iodine or bromine that react with the peracetic acid in the sample solution, reducing its concentration, and thereby reducing its disinfecting/sterilizing effect.

In the fields of food and medicine, where this sort of sample solution is often used, iodine and bromine contamination of a sample may have a toxic contaminating effect on living bodies, as well. Furthermore, since iodine and bromine have a strong residual tendency, equipment for handling samples with leaked iodine and bromine may remain contaminated in the long term, even after washing.

Finally, bromine has the property of easily gasifying under an acid environment. Thus, in the event that it leaks into an acid solution containing peracetic acid, toxic bromine gas is produced. To avoid accidents, operators are burdened by the need for extreme caution when handling a peracetic acid concentration meter.

The membrane covered type sensor described in Patent Literature 2, also presents a challenge. In this technology, as the distance between the membrane and the electrode (working electrode) is shortened, the time required for a sample substance to permeate the membrane and reach the surface of the working electrode is shortened, and the responsiveness of the sensor is increased. For this reason, in the above-described membrane covered type sensor, it is desirable to arrange the working electrode and the membrane to be in direct contact, or as close as possible to one another.

However, in cases where the membrane is formed of material with superior flexibility, such as silicon rubber, as is the case in the membrane covered type sensor described in Patent Literature 2, the membrane and the electrode surface might come in direct contact without leaving any space in between them. In the absence of a space in between the membrane and the electrode, the inter solution might not reach the surface of the working electrode, and the specific substance being tested specific (in Patent Literature 2, hydrogen peroxide) will fail to react with the iodine or bromine in the internal solution at the surface of the working electrode. Consequently, the sensitivity of the sensor will be decreased.

The present invention is made in consideration of the above-described problems. The main objective of the present invention is thus to provide a membrane covered type peracetic acid concentration meter that can avoid the various problems described above, even in the event of a leak of inter solution into the sample solution.

In addition, the invention aims at providing a membrane covered type sensor making it possible to improve sensor responsiveness without deteriorating sensor sensitivity.

Solution to Problem

The peracetic acid concentration meter of the present invention is a membrane covered type peracetic acid concentration meter that measures the concentration of peracetic acid in a sample solution, and includes: a membrane that allows peracetic acid to permeate; an internal solution that dissolves peracetic acid having permeated the membrane; a working electrode, and counter electrode that are immersed in the internal solution; an internal solution that is a buffer solution, having a buffering action on hydrogen ion concentration.

In the above-described peracetic acid concentration meter, since the internal solution used is a buffer solution having a buffering action on hydrogen ion concentration, even if the internal solution leaks toward the sample solution side during the measurement of the peracetic acid in a sample solution, the internal solution will not have a disinfecting/sterilizing effect on the sample solution. This is because the peracetic acid contained in the sample solution will not react with the buffer solution. Therefore, the peracetic acid concentration in the sample solution will not be affected, even in the event of a leak.

Furthermore, since the internal solution used in the present invention does not contain iodine or bromine, the inherent risks associated with iodine or bromine contamination, such as toxicity to living bodies, and a residual tendency that can contaminate materials and equipment long term, are completely avoided. Therefore even if the internal solution leaks into a sample solution used in the fields of medicine and food, there will be no effect on living bodies.

Finally, since bromine is not present in the present invention's internal solution, there is no risk of formation of toxic gasses, which significantly improves the safety of the work environment for operators.

The current invention is also designed to avoid acidification of the internal solution, and to consequently ensure accurate measurement.

During operation, the peracetic acid in the sample solution changes to acetic acid at the surface of the working electrode, and as this reaction takes place, the amount of acetic acid increases in the internal solution, causing the internal solution to gradually acidify. In the current invention, however, since the internal solution consists of a buffer solution, the internal solution is prevented from acidifying. Consequently, accurate measurement can be performed.

In a specific embodiment of the intermediate membrane of the peracetic acid concentration meter according to the present invention, an embodiment where an internal solution that does not contain a material reactive with peracetic acid can be cited.

In the above-described configuration, even if the internal solution leaks into the sample solution, the internal solution will not react with the peracetic acid in the sample solution. Thus, the concentration of the peracetic acid in the sample solution will not be affected, and the disinfecting/sterilizing effect of the peracetic acid will not change.

In a specific embodiment of the intermediate membrane of the peracetic acid concentration meter according to the present invention, an embodiment where a membrane made from a material containing silicon, fluororesin, or polyethylene, can be cited.

In a specific embodiment of the intermediate membrane of the peracetic acid concentration meter according to the present invention, an embodiment where a working electrode that is in contact with the membrane via an intermediate membrane, and has wettability with respect to the internal solution, can be cited.

It is known that as the working electrode is brought closer to the membrane, responsiveness to a reaction between the internal solution and peracetic acid in the sample having permeated the membrane at the surface of the working electrode, is made quicker. However, bringing the working electrode into contact with the membrane gives rise to the problem that depending on the material of the membrane, contact between the membrane and the electrode surface may create a situation where there is no space in between the two for the internal solution to occupy. In the absence of space between the membrane and the electrode, a sufficient supply of internal solution may not be available at the surface of the working electrode. In turn, a reaction between the internal fluid and sample is blocked from taking place at the surface of the working electrode, and consequently the sensitivity of the device deteriorates.

However, in the above-described configuration, since the working electrode is in contact with the membrane via an intermediate membrane having wettability with respect to the internal solution, the internal solution can be supplied to the working electrode from liquid layers formed on the surfaces of the intermediate membrane, regardless of the material of the membrane. Therefore, it is possible to prevent blockage of the reaction at the surface of the working electrode, and to avoid the deterioration of the sensitivity of the device. Further, by making the thickness of the intermediate membrane thinner, the working electrode can be brought closer to the membrane, which improves the responsiveness of the working electrode as well. Consequently, the responsiveness of the working electrode can be improved without sacrificing reactivity at the working electrode.

In a specific embodiment of the intermediate membrane of the peracetic acid concentration meter according to the present invention, an embodiment where the intermediate membrane has a porous membrane can be cited. As the intermediate membrane having a porous membrane, a porous film, a microperforated film, a microporous film, or the like can be cited. Also, a polymer can be used for the intermediate membrane.

By configuring the intermediate membrane as described, the internal solution not only covers the surface of the intermediate membrane, but also permeates through the fine pores of the intermediate membrane. As a result, the distance required for peracetic acid dissolved in the internal solution to reach the working electrode can be shortened, making reactivity at the surface of the working electrode quicker.

In another specific embodiment of the peracetic acid concentration meter according to the present invention, an embodiment where a protective film is provided on the surface of the membrane on the sample solution side, so as to avoid an area where the membrane is in contact with the intermediate membrane, can be cited.

In such a configuration, the protective film can prevent damage to the membrane, and prevent the internal solution from leaking toward the sample solution side. Also, in such a configuration, impurities and the like, in the sample solution, can be prevented from intruding into the internal solution through the membrane. Consequently, measurement accuracy can be increased.

The membrane covered type sensor of the present invention is a membrane covered type sensor used to sense a specific substance in a sample solution, and includes: a membrane that allows the specific substance in the sample solution to permeate; an internal solution that dissolves the specific substance having permeated the membrane; and a working electrode and an counter electrode that are immersed in the internal solution. In addition, the working electrode is in contact with the membrane via an intermediate membrane having wettability with respect to the internal solution.

In the above-described configuration, despite bringing the working electrode and the membrane closer to each other, since the working electrode is in contact with the membrane via the intermediate membrane, the intermediate membrane can prevent the working electrode and the membrane from coming in close contact with each other in a manner that leaves no space in between them. Also, since the intermediate membrane has wettability with respect to the internal solution, and since on the surfaces of the intermediate membrane liquid layers of the internal solution are formed, the specific substance dissolved in the internal solution can be supplied to the surface of the working electrode from the liquid layers. Consequently, the membrane and the working electrode can be brought closer to each other in order to improve responsiveness of the sensor, without the undesirable consequence of blocking the reaction at the surface of the working electrode and thereby deteriorating the sensitivity of the sensor.

In a specific embodiment of the membrane covered type sensor according to the present invention, an embodiment where the intermediate membrane has an elastic modulus larger than that of the membrane, can be cited.

In such a configuration, since the intermediate membrane has a high degree of elasticity compared with the membrane, the intermediate membrane itself can reliably prevent the membrane from coming in close contact with the working electrode, and thereby the potential for sensor sensitivity deterioration is prevented, and the sensor is able to operate effectively.

As the membrane covered type sensor of the present invention, a membrane covered type sensor featuring an intermediate membrane having a thickness of 1 µm to 100 µm can be cited.

In such a configuration, the time required for the internal solution to permeate the intermediate membrane can be shortened to increase a speed at which the internal solution is supplied to the working electrode, and therefore responsiveness of the working electrode can be made quicker. Note that in the case of setting the thickness of the intermediate membrane to greater than 100 µm, the responsiveness of the working electrode is deteriorated, whereas in the case of setting the thickness of the intermediate membrane with less than 1 µm, the intermediate membrane becomes difficult to handle.

As the membrane covered type sensor of the present invention, a membrane covered type sensor featuring an intermediate membrane having fine pores can be cited.

In such a configuration, the internal solution dissolving the specific substance is supplied to the surface of the working electrode through the fine pores provided in the intermediate membrane, and therefore the distance required for the specific substance to reach the surface of the working electrode can be further shortened to improve responsiveness of the sensor. Also, the internal solution can be supplied to the surface of the working electrode through the fine pores, and therefore the internal solution can be stably supplied to the surface of the working electrode to make the sensor stable. As the intermediate membrane having fine pores, for example, a porous film, a microperforated film, a microporous film, or the like can be cited.

In another specific embodiment of the membrane covered type sensor according to the present invention, an embodiment where the pore diameter of the fine pores of the porous film is 0.05 µm to 100 µm can be cited.

Meanwhile, in a conventional membrane covered type sensor, air bubbles included in a sample solution and/or air bubbles attached to the sensor, intrude into the sensor through a membrane having gas permeability, or by being produced by an oxidation-reduction reaction at the surface of a working electrode. These air bubbles can remain between the working electrode and the membrane, blocking the internal solution and sample solution from reaching and reacting at the surface of the working electrode, thereby giving rise to the problem of deteriorating sensitivity of the sensor.

However, in the membrane covered type sensor of the present invention, since the intermediate membrane is arranged between the working electrode and the membrane is the porous film, and the pore diameter of the fine pores of the porous film is 0.05 µm to 100 µm, the pore diameter of the fine pores is sufficiently smaller than the size of air bubbles (having a size of 500 µm or more), and therefore the air bubbles never remain in the fine pores. For this reason, even in the case where air bubbles are produced, the internal solution can be supplied to the surface of the working electrode through the fine pores, and therefore deterioration in sensitivity of the sensor can be prevented without blocking the reaction at the surface of the working electrode.

As still another embodiment of the membrane covered type sensor according to the present invention, an embodiment where the intermediate membrane is made from a polymer and the membrane is made from a material containing silicon, fluororesin, or polyethylene can be cited.

As yet another embodiment of the membrane covered type sensor according to the present invention, an embodiment where the working electrode is in contact with the membrane via the intermediate membrane, and applies pressure on the membrane that stretches the membrane, can be cited.

In such a configuration, the distance between the working electrode and the membrane can be further shortened, and therefore responsiveness at the surface of the working electrode can be further improved.

Finally, a liquid analyzer using the above-described membrane sensor is also one aspect of the present invention.

Advantageous Effects of Invention

According to the present invention, even if an internal solution leaks into a sample solution, an effect on the sample solution or on living bodies can be prevented. Also, sensor responsiveness can be improved without deteriorating sensor sensitivity.

DESCRIPTION OF EMBODIMENTS

In the following, a peracetic acid concentration meter of the present invention will be described with reference to the drawings.

Figure 1:
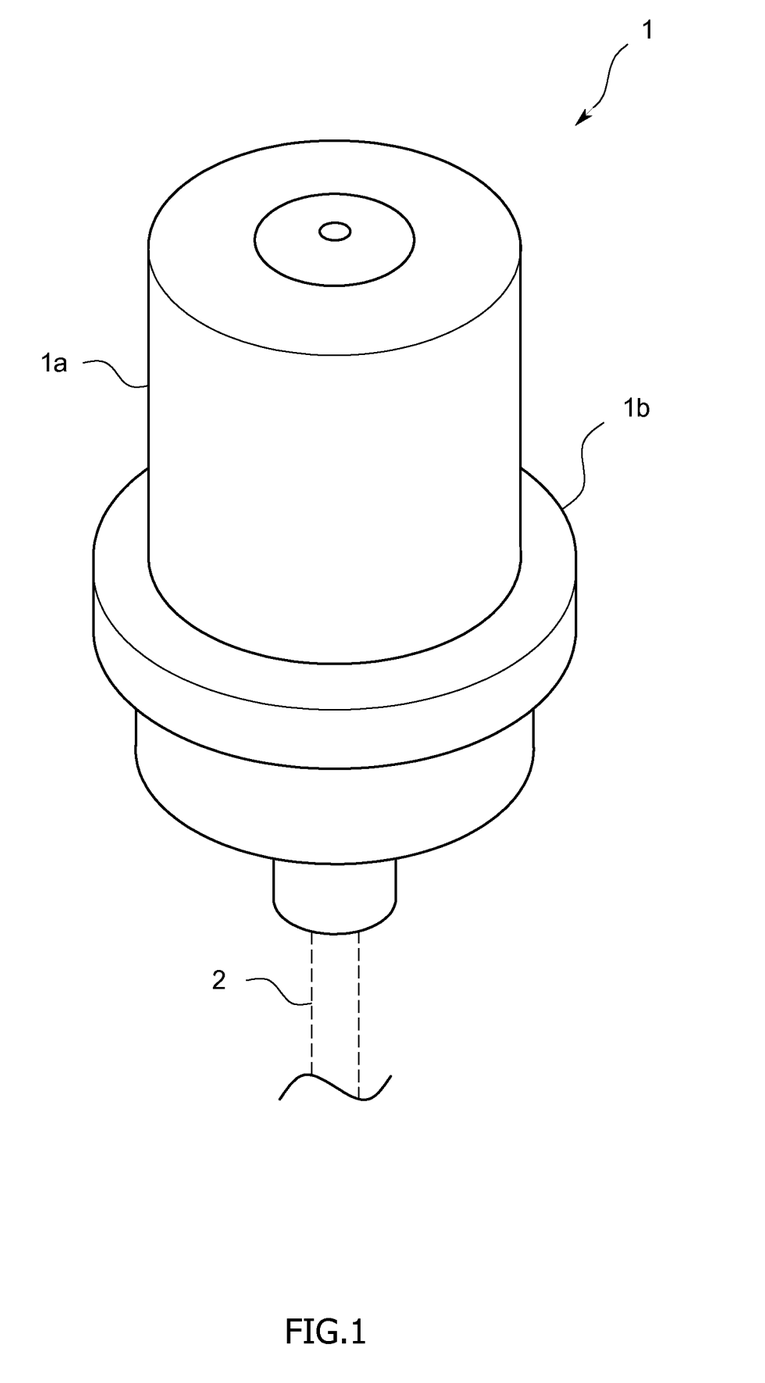
FIG. 1 is a schematic diagram illustrating a peracetic acid concentration meter in the present embodiment.

A peracetic acid concentration meter in the present embodiment is a membrane covered type peracetic acid concentration meter adapted to measure the concentration of peracetic acid used for, for example, chemical solutions in the field of medicine and food. As illustrated in FIG. 1, the peracetic acid concentration meter in the present embodiment includes: a sensor part 1 that measures the peracetic acid concentration; and an unillustrated instrument body part that is electrically connected to the sensor part 1 via a waterproof cable 2. In addition, the peracetic acid concentration meter is one that measures the concentration of peracetic acid contained in a sample solution by immersing the sensor part 1 in the sample solution.

Figure 2:
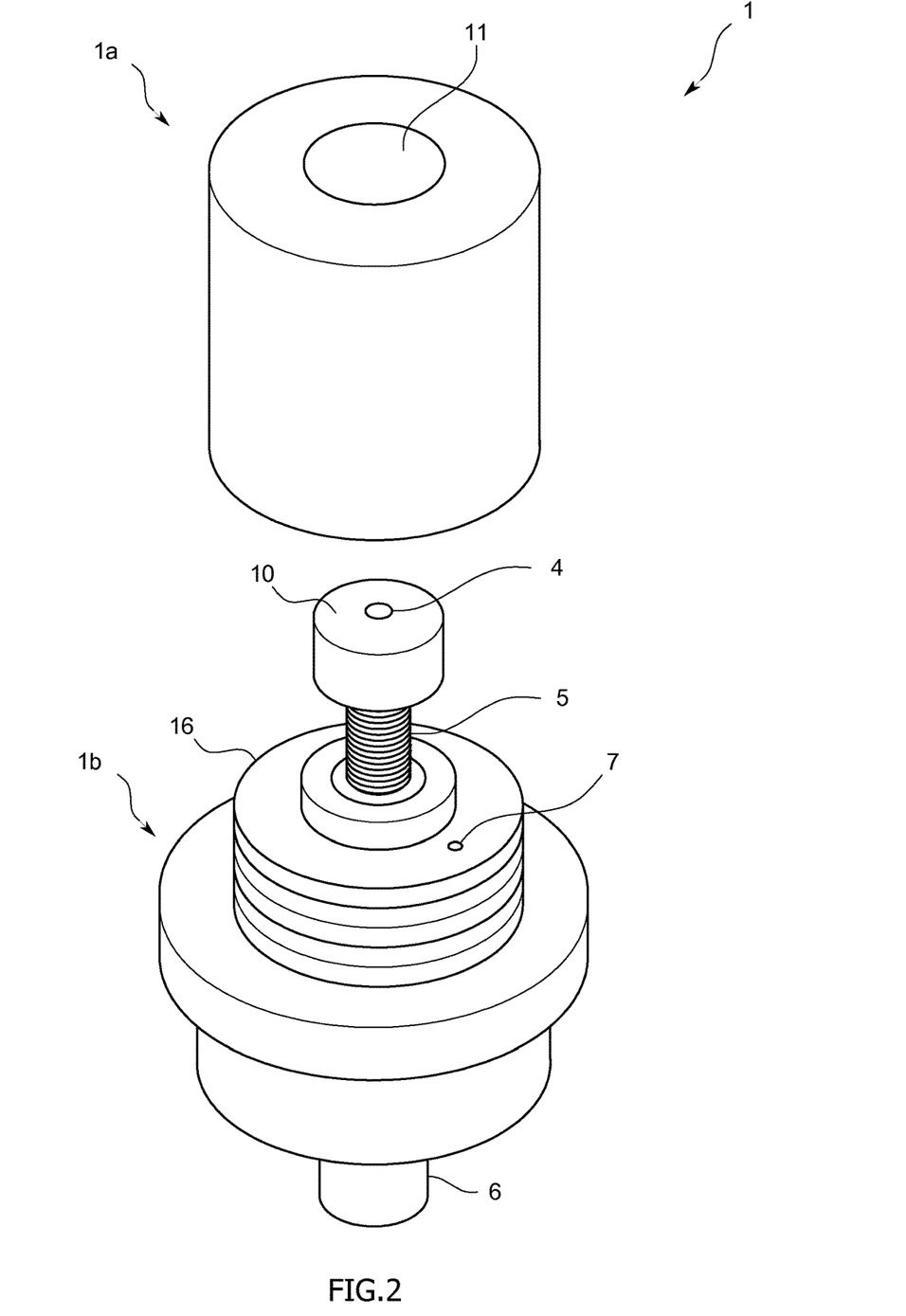
FIG. 2 is a schematic diagram illustrating a sensor part in the present embodiment.
Figure 3:
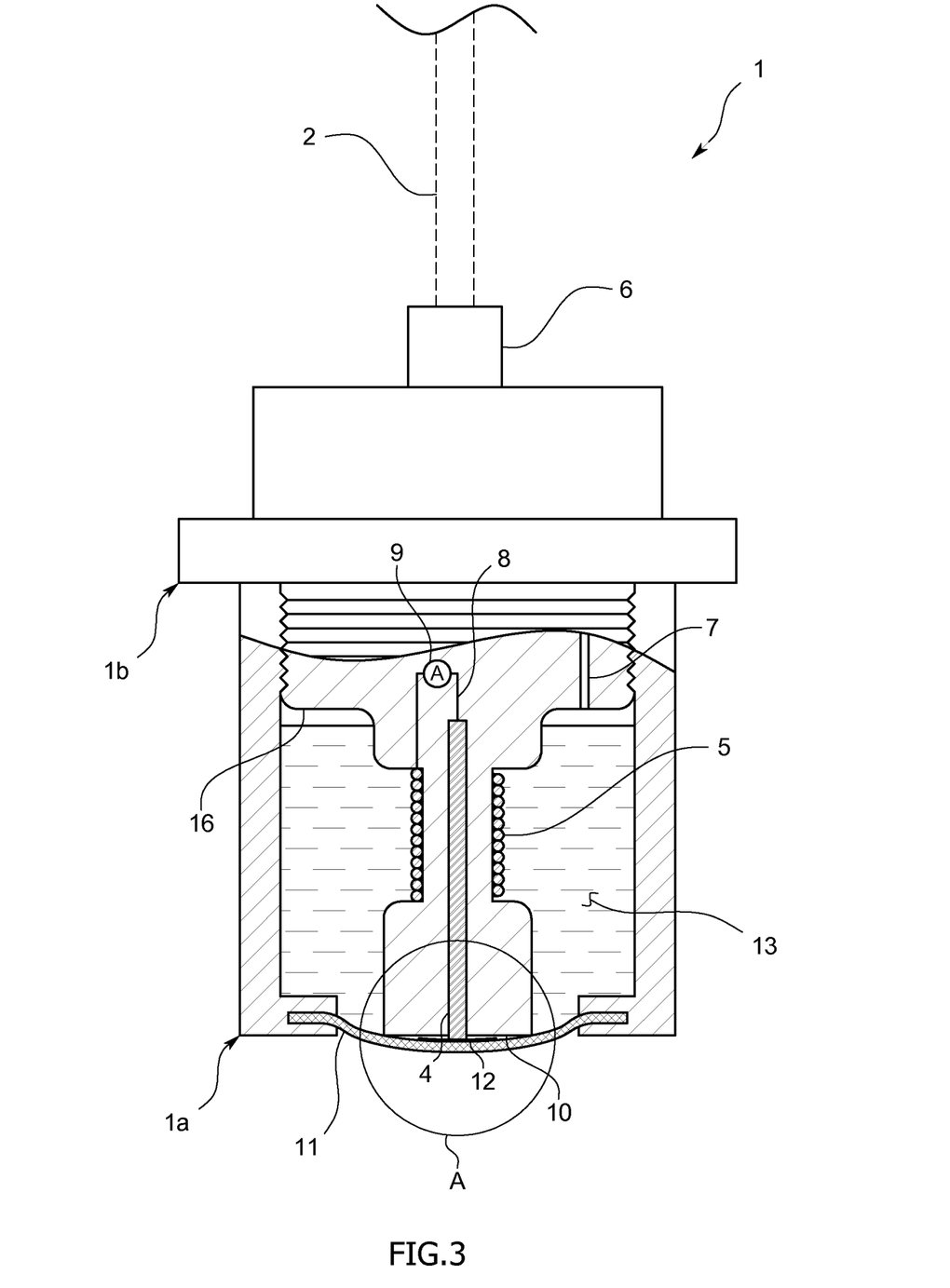
FIG. 3 is a schematic cross-sectional view illustrating the sensor part in the present embodiment.

As illustrated in FIGS. 2 and 3, the sensor part 1 includes: a container 1a for containing an internal solution 13; and a lid part 1b for sealing the container 1a.

The container 1a is of a hollow cylindrical shape of which one end surface is opened and the other end surface is closed, and when attaching the lid part 1b to the container 1a, a containing space is formed inside the container 1a. Also, on the inner wall near the opened end, an unillustrated thread for attaching the lid part 1b is formed. In addition, in a part of the other end surface, a through-hole is provided, and a membrane 11 is provided so as to block the through-hole.

The membrane 11 is permeable to the peracetic acid in the sample solution, and is formed from a material containing, for example, silicon, fluororesin, or polyethylene. For example, as a fluororesin, Teflon (registered trademark) or the like can be used. Also, the material having a thickness of, for example, 10 μm to 200 μm as a film thickness of the membrane 11 can be used.

The lid part 1b is adapted to seal the container 1a. In the state where the container 1a is sealed, the retaining member 16, which contains a working electrode 4 and a counter electrode 5, is contained in the space between lid part 1b and container 1a. Furthermore, in this state, the end tip of the retaining member 16 protrudes slightly from the outer surface of the container.

Also, the lid part 1b is attached to a connector part 6 that connects the sensor part 1 to the instrument body part through waterproof cable 2.

The retaining member 16 is formed from an insulating material, and as illustrated in FIG. 3, it retains the working electrode 4 by surrounding the working electrode 4 as well as retaining the counter electrode 5 that is wounded around the retaining member 16. Also, the retaining member 16 has a spiral groove for attaching the lid part 1b to the container 1a, and by fitting the unillustrated thread provided on the container 1a side into the spiral groove, the lid part 1b can be attached to the container 1a. Further, the retaining member 16 includes an air hole 7 for discharging air to the outside. In addition, one opening end of the air hole 7 is provided with a filter for gas-liquid separation.

The working electrode 4 is formed from an electrically conductive material such as gold or platinum, and in the present embodiment, as illustrated in FIGS. 2 and 3, it has a rod shape. Also, the working electrode 4 is positioned so as to slightly protrude from a fore end surface 10 of the retaining member 16 in a state of being retained by the retaining part 16. Further, the surface of the working electrode 4 has unillustrated minute unevenness.

The counter electrode 5 is formed from an electrically conductive material such as platinum or silver-silver chloride (Ag/AgCl), and in the present embodiment it is formed of a platinum wire.

The working electrode 4 and the counter electrode 5 are, as illustrated in FIG. 3, connected to each other via a lead 8. Voltage is supplied through the lead 8 by an unillustrated power supply means provided outside. Also, the lead 8 is provided with an ammeter 9, adapted to sense electrical current flowing through the lead 8. Note that the lead 8 and the ammeter 9 may be provided outside the lid part 1b.

Further, as illustrated in FIG. 3, the internal solution 13 is contained in the space formed between the lid part 1b and the container 1a, in the state where the lid part 1b is attached to the container 1a.

As the internal solution 13, a buffer solution having a buffering action on hydrogen ion concentration is used. The internal solution 13 does not contain any substance that is reactive with peracetic acid. In the present embodiment, the internal solution 13 consists only of the buffer solution. An acid buffer solution or a neutral buffer solution are preferable. However, the buffer solution is not limited to a particular solution type. The buffer solution should have a buffering action, therefore an acid buffer solution, neutral buffer solution, alkali buffer solution, or the like can be used. In the present embodiment, for example, a phosphate buffer solution, acetic acid buffer solution, tris buffer solution, borate buffer solution, citrate buffer solution, or the like can be used.

Also, on the container 1a side of the membrane 11, an intermediate membrane 12 having wettability with respect to the internal solution 13 is provided. The intermediate membrane 12 is arranged between the membrane 11 and the working electrode 4, in the state where the container 1a is attached to the lid part 1b. For the intermediate membrane 12, a material having an elastic modulus (bulk modulus) larger than that of the membrane 11 can be used. Example materials that can be used for intermediate membrane 12 include polymers such as: polycarbonate, polytetrafluoroethylene (PTFE), mixed resin in which polyethylene and polyimide are mixed, polyimide, cellulose, and other similar materials. Note that wettability refers to property of having affinity between the intermediate membrane 12 and the internal solution 13, which leads the internal solution 13 to accumulate on, and become absorbed by the intermediate membrane 12, thereby forming a liquid layer of the internal solution 13 on the surface of the intermediate membrane 12. Also, as the intermediate membrane 12, a film having a thickness of 1 μm to 100 μm can be used.

In addition, the intermediate membrane 12 is configured as a porous film in which innumerable fine pores having a pore diameter of 0.05 μm to 100 μm are formed. The pores being sufficiently smaller than the size (500 μm or more) of bubbles of an enzyme or the like.

Figure 4:
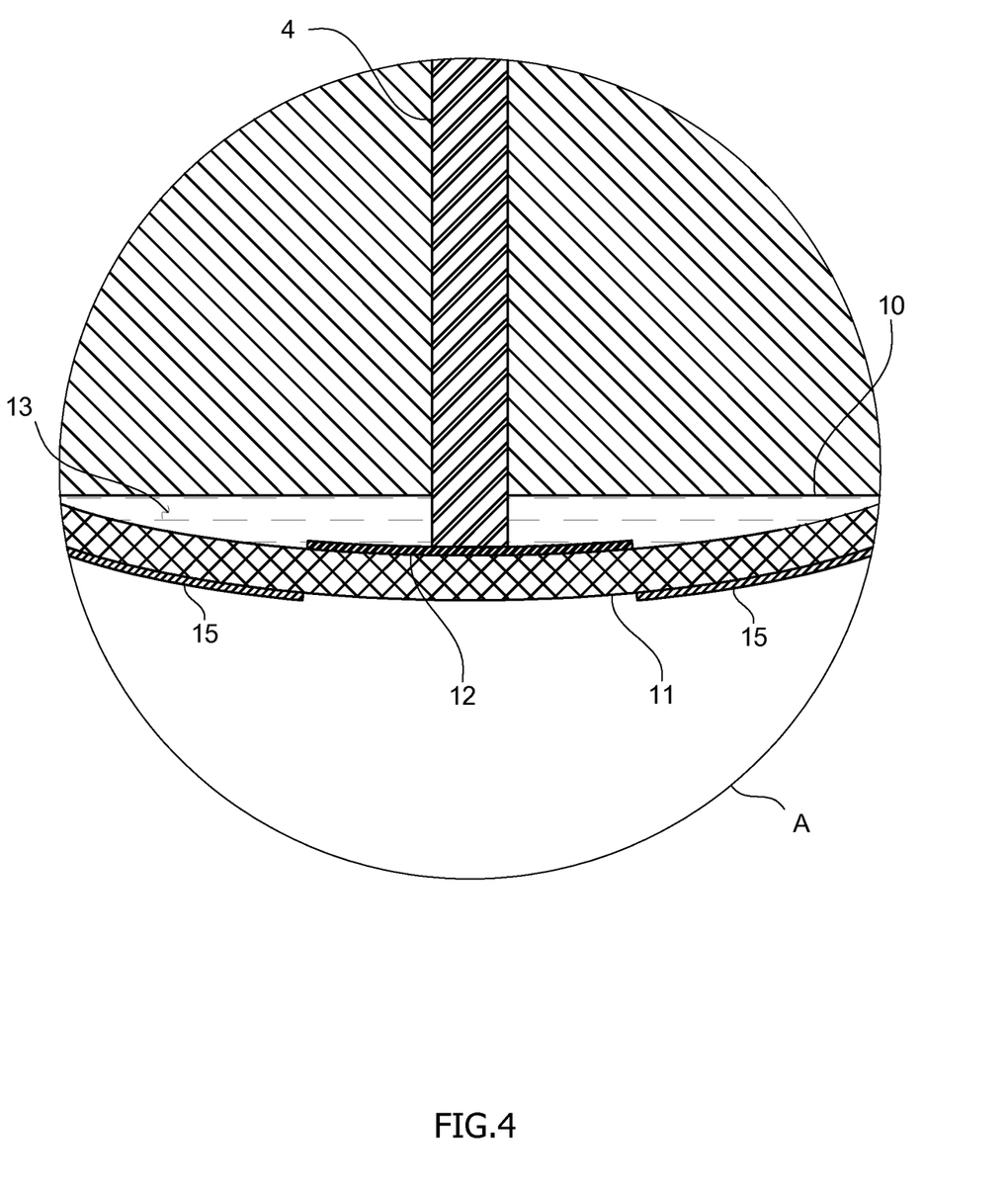
FIG. 4 is a schematic enlarged view that enlarges the part A in FIG. 3 in the present embodiment.

Also, as illustrated in FIG. 4, on a surface of the membrane 11 on the sample solution side, a protective film 15 is provided so as to avoid an area where the membrane 11 is in contact with the intermediate membrane 12. The material for the protective film 15 is not particularly limited. For example, polypropylene, PFA, PET, or the like can be used.

The instrument body part displays measurement data or the like from the sensor part 1, and actuates the sensor part 1 in accordance with a signal inputted by an operator. The instrument body part is realized by the use of physical components including for example: analog circuits, digital circuits such as CPU or memory, and more.

The operation of the peracetic acid concentration meter of the present invention, in the above described configuration, is described below.

When attaching the lid part 1b to the container 1a, the working electrode 4 contacts with the membrane 11 via the intermediate membrane 12. In this state, since the working electrode 4 is arranged so as to slightly protrude from the fore end surface 10 of the retaining member 16, the working electrode 4 is in contact with the membrane 11 via the intermediate membrane 12, and applies pressure on the membrane 11 that stretches the membrane 11.

Figure 5:
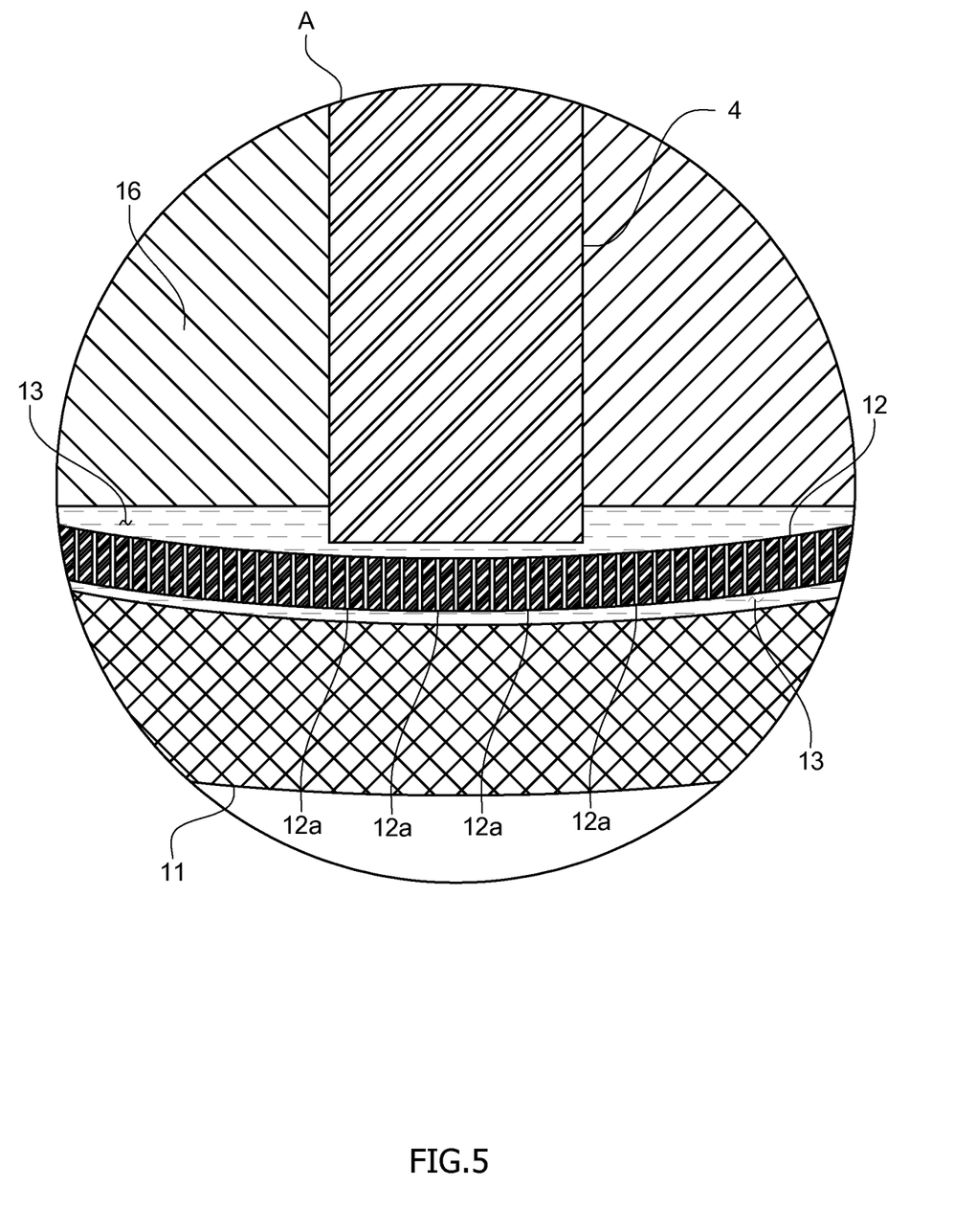
FIG. 5 is a schematic enlarged view that further enlarges the part A in FIG. 3 in the present embodiment.

Also, the internal solution 13 is contained between the container 1a and the lid part 1b. As illustrated in FIG. 5, the contained internal solution 13 fills a minute gap between the membrane 11 and the intermediate membrane 12, as well as a minute gap between the intermediate membrane 12 and the working electrode 4. Note that since the intermediate membrane 12 has wettability with respect to the internal solution 13, liquid layers of the internal solution 13 are formed on the surface of the intermediate membrane 12. Also, since the intermediate membrane 12 is a porous film, the internal solution 13 intrudes into the intermediate membrane 12 through the fine pores 12a formed in the intermediate membrane 12. For this reason, the working electrode 4 is in contact with the intermediate membrane 12 via one of the liquid layers, and the intermediate membrane 12 is also in contact with the membrane 11 via the other liquid layer. However, the above-described liquid layers are both very thin layers, and therefore the working electrode 4 can be considered as being substantially in contact with the membrane 11 via the intermediate membrane 12.

When immersing the sensor part 1 into the sample solution in this state, the peracetic acid contained in the sample solution permeates the membrane 11, and is dissolved in the internal solution 13 inside the sensor part 1. Further, when the predetermined voltage is applied between the working electrode 4 and the counter electrode 5 by the unillustrated power supply means through the lead 8, the following reactions take place on the surfaces of both electrodes:

Working electrode 4: $CH_3COOOH(PAA)+2H^{+}+2e^{-} \rightarrow CH_3COOH+H_2O$

Counter electrode 5: $2H_2O+O_2+4e^{-} \leftarrow 4OH^{-}$

When the above-described oxidation-reduction reaction takes place, an electric current is produced. The value of the electric current is measured by the ammeter 9, and an output signal indicating the current's value is transmitted to the instrument body part. Upon receipt of the output signal indicating the current's value, the instrument body part calculates the concentration of the peracetic acid contained in the sample solution from the output signal, with reference to a predetermined conversion expression or conversion table, and displays the peracetic acid concentration.

The peracetic acid concentration meter in the present embodiment in the configuration described above has the following remarkable effects.

Since the internal solution 13 being used is a buffer solution having a buffering action on hydrogen ion concentration, even if the internal solution 13 leaks towards the sample solution side during the peracetic acid concentration measurement, the peracetic acid contained in the sample solution does not react with the buffer solution. Therefore, peracetic acid concentration is not decreased, and the disinfecting/sterilizing effect of the sample solution is maintained.

Also, since iodine or bromine are not present in the buffer solution, all risks associated with iodine or bromine contamination are avoided. This makes the present invention particularly suitable for use in the fields of medicine and food, where iodine and bromine can have a negative impact on living bodies.

The absence of bromine from the buffer solution also means that the solution does not produce toxic gas. This significantly improves the safety of the work environment and reduces the psychological burden on operators.

Peracetic acid in the sample solution changes to acetic acid at the surface of the working electrode 4, in accordance with the above-described reaction. As the reaction proceeds, the amount of acetic acid in the internal solution 13 increases, and the internal solution can potentially acidify. However, since the internal solution 13 used in the present embodiment is a buffer solution, the undesirable acidification of the internal solution is prevented.

Further, the lid part 1b includes an air hole 7. When attaching the lid part 1b to the container 1a, the internal pressure between the container 1a and the lid part 1b increases. Excess pressure is therefore released through the air hole 7. Still further, the air hole 7 also serves to release air bubbles (gas) that tend to form inside the sensor, and may cause system failure if not released.

In addition, a protective film 15 is provided on the surface of the membrane 11 on the sample solution side. The protective film 15 limits protects the membrane 11 from damage, such as tearing, and prevents the internal solution 13 from leaking into the sample side. The protective film 15 also help to prevents particles and other contaminants in the sample solution from intruding into the internal solution 13 through the membrane 11. The protective film 15 is ideally made of a highly elastic material, which further improves the protection of membrane 11 from damage. Thus the protective film 15 contributes to improved measurement accuracy.

Still further, since the membrane 11 is formed from a material containing silicon, fluororesin, or polyethylene, even in the case where the internal solution 13 consists of the buffer solution, the concentration of peracetic acid can be measured.

In order to verify the above-described effects, the following test was performed.

This test intends to examine a membrane material that makes it possible to measure the concentration of peracetic acid without decreasing responsiveness of a working electrode, even in the case where an internal solution consists of a buffer solution in a peracetic acid concentration meter adapted to measure the concentration of peracetic acid.

As sample solutions used for the test, a peracetic acid solution and pure water were used.

Also, as samples used for the test, three peracetic acid concentration meters were prepared, each having a sensor part including: a membrane; an internal solution that dissolved peracetic acid having permeated the membrane; and a working electrode and an counter electrode that were immersed in the internal solution.

Each of the samples is described in detail below.

Peracetic acid concentration meter A used: a porous film made from polybutylene terephthalate (PBT) for its membrane; a phosphate buffer solution for its internal solution; a gold working electrode; and a platinum counter electrode.

Peracetic acid concentration meter B was identical to Peracetic acid concentration meter A, with the exception of the membrane used. The membrane used in the peracetic acid concentration meter B was a porous film made from silicon.

Peracetic acid concentration meter C was identical to Peracetic acid concentration meters A and B, with the exception of the membrane used. The membrane used in the peracetic acid concentration meter C is a PE based thermoplastic elastomer resin.

Figure 6:
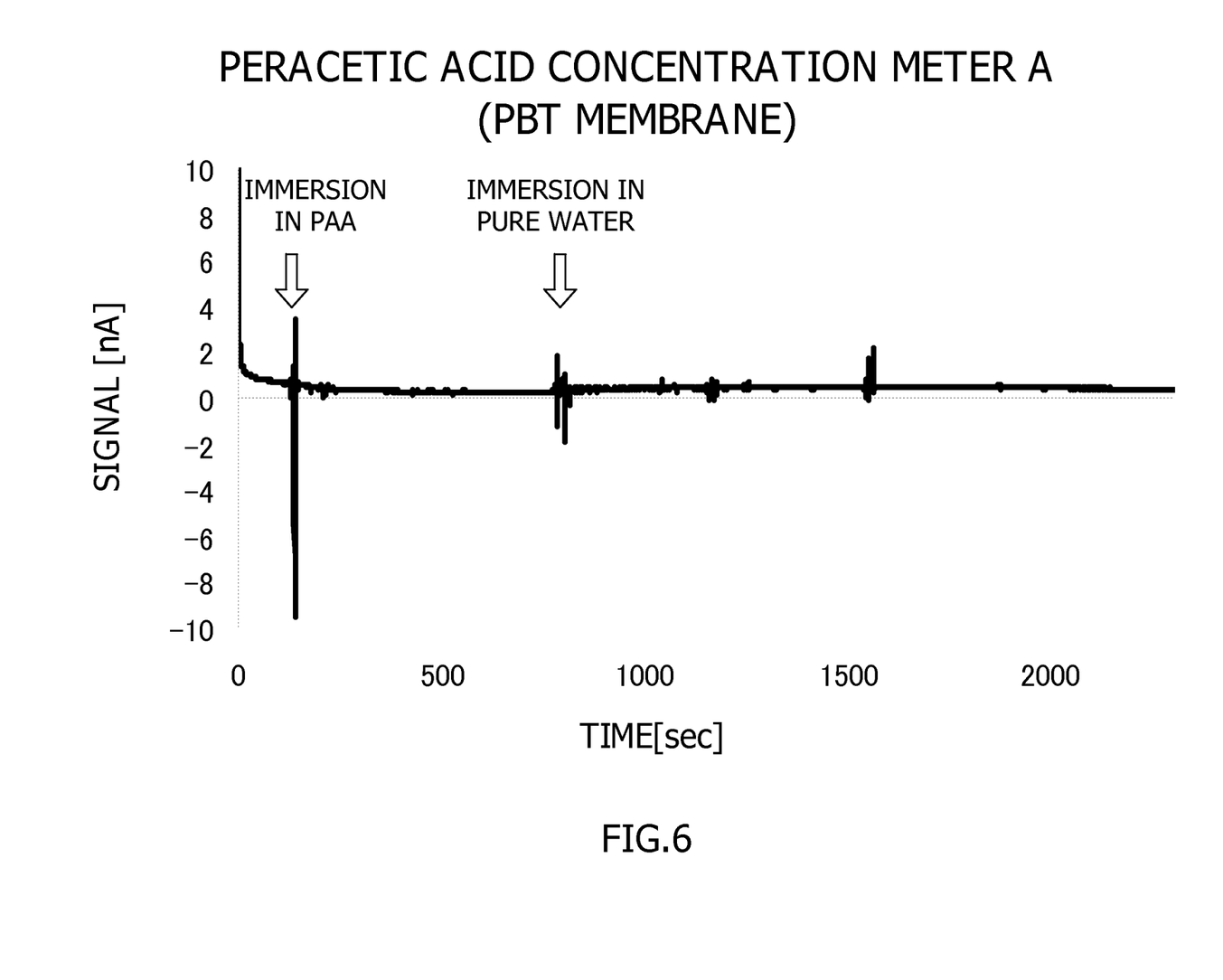
FIG. 6 is a graph illustrating a current value of a peracetic acid concentration meter A and response time.
Figure 7:
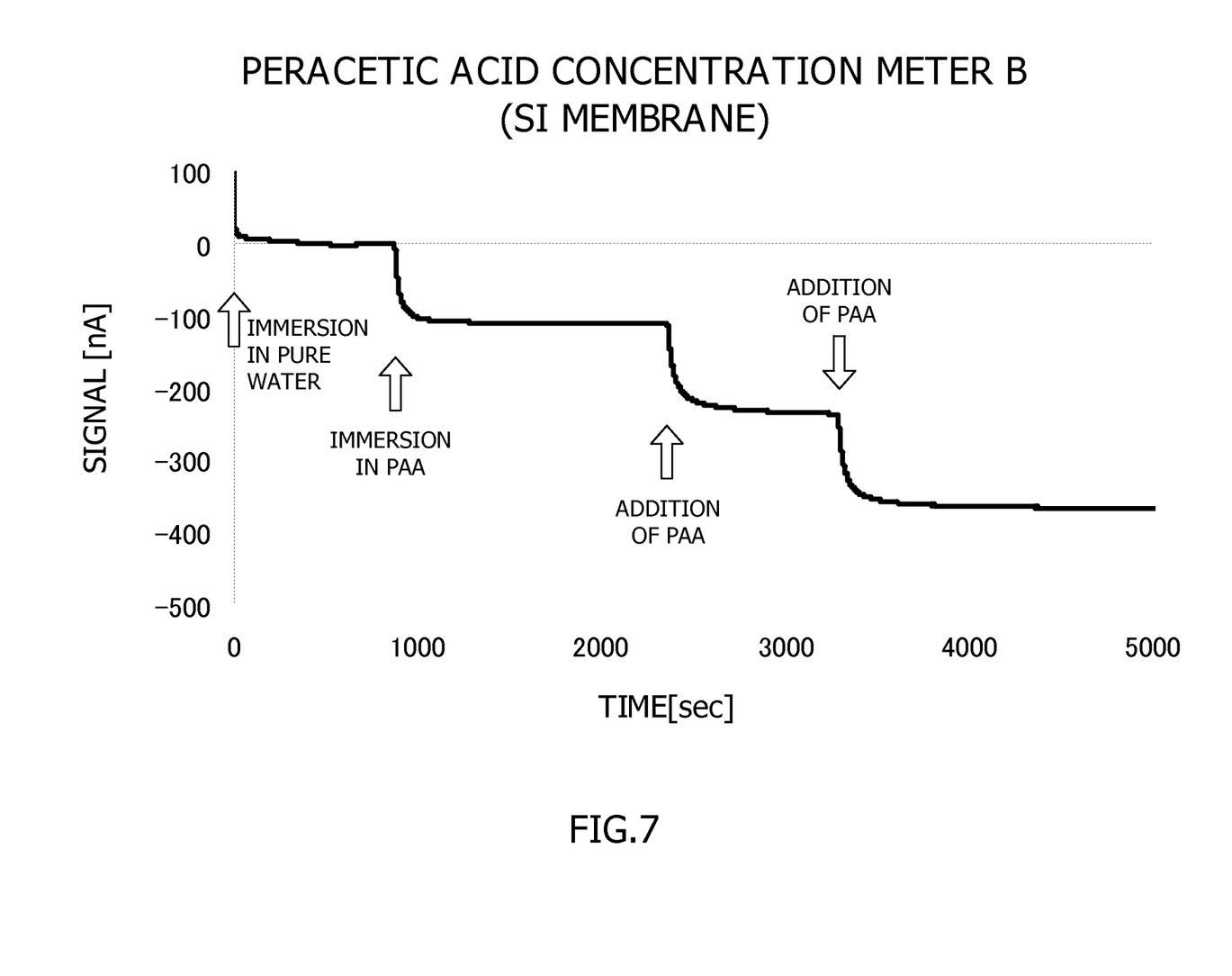
FIG. 7 is a graph illustrating a current value of a peracetic acid concentration meter B and response time.
Figure 8:
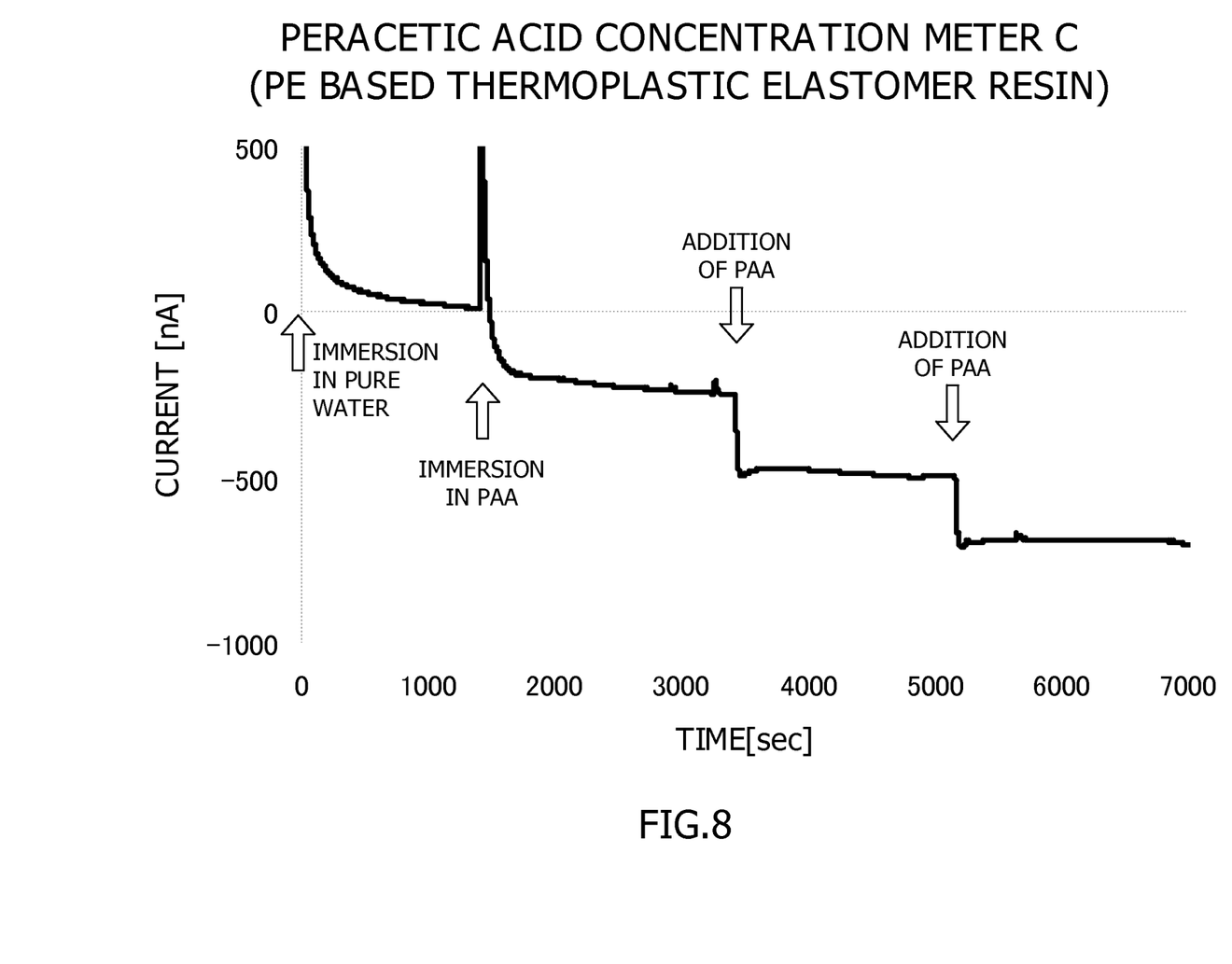
FIG. 8 is a graph illustrating a current value of a peracetic acid concentration meter C and response time.

The above-described peracetic acid concentration meters A to C were used to measure a current value and a current flow time at the time of immersion in the sample solution. FIGS. 6 to 8 illustrate the results of the measurement.

FIG. 6 illustrates the test result of the peracetic acid concentration meter A. As illustrated in FIG. 6, the peracetic acid concentration meter A could not measure any current value in both cases of immersion in the peracetic acid solution and immersion in the pure water.

The reason why peracetic acid concentration meter A could not measure any current value may be that the peracetic acid in the peracetic acid solution could hardly permeate the membrane.

FIG. 7 illustrates the test result of the peracetic acid concentration meter B. As illustrated in FIG. 7, when immersed in pure water, the peracetic acid concentration meter B did not sense an electrical current. On the other hand, in the case of immersion in the peracetic acid solution, the peracetic acid concentration meter B sensed an electric current that reached approximately −100 nA, and was maintained for at least a predetermined period of time to ensure stability.

When peracetic acid was added to the peracetic acid solution being tested by peracetic acid concentration meter B, the value of the electrical current changed to approximately −200 nA, and was maintained for at least a predetermined period of time to ensure stability. When peracetic acid was added to the peracetic acid solution being tested by peracetic acid meter B for a second time, the value of current changed to approximately −350 nA, and was maintained for at least a predetermined period of time to ensure stability.

The results in the case of the peracetic acid concentration meter B may be explained as follows. The peracetic acid in the peracetic acid solution permeated the membrane and was then dissolved in the internal solution. Thereby, at the surfaces of the working and counter electrodes, an oxidation-reduction reaction continuously took place, maintaining a constant electric current value for a predetermined time. The results indicate that the peracetic acid concentration meter B was able to stably measure an electric current value, and accurately measure peracetic acid concentration.

FIG. 8 illustrates the test result of the peracetic acid concentration meter C. As illustrated in FIG. 8, the peracetic acid concentration meter C did not sense anything in the case of immersion in the pure water, but in the case of immersion in the peracetic acid solution, it sensed a stable value of current of approximately −100 nA, which was kept for a predetermined time. Also, when adding peracetic acid to the peracetic acid solution, the value of current changed to approximately −500 nA, which was kept for a predetermined time. Further, when adding peracetic acid to the peracetic acid solution a second time, the value of current changed to approximately −750 nA, which was kept for a predetermined time.

The results in the case of the peracetic acid concentration meter C can be explained as follows: as in the case of peracetic acid concentration meter B, peracetic acid in the peracetic acid solution permeated the membrane and an oxidation-reduction reaction took place at the surfaces of the working and counter electrodes. The results indicate that the peracetic acid concentration meter C can measure a current value, and peracetic acid concentration value.

The results above demonstrate that by forming the membrane 11 from a material containing silicon, fluororesin, or polyethylene, the concentration of peracetic acid can be measured reliably.

Note that the above-described test results were obtained for the peracetic acid concentration meters not including an intermediate membrane 12. However, similar results were also obtained for peracetic acid concentration meters including an intermediate membrane 12.

The peracetic acid concentration meter in the present embodiment has the following remarkable effects:

The peracetic acid concentration meter in the present embodiment prevents the membrane 11 and the working electrode 4 from coming in direct contact by the use of intermediate membrane 12, which is located in between the membrane 11 and the working electrode 4 and intermediate membrane 12 also has the characteristic of having wettability to fluids, thus ensuring a stable and immediate supply of internal solution 13 at its surface and improving the response.

Intermediate membrane 12 is a thin porous film through which the internal solution, so maintains a minimal distance between the membrane 11 and the working electrode 4 that ensures a stable flow of internal solution 13 to the surface of working electrode 4 and fine pores provided in intermediate membrane 12 is stably supplied internal solution 13 to the surface of the electrode 4, making the sensor part 1 highly sensitive, responsive, and reliable.

In order to verify the above effects, the following tests were performed.

These tests intended to evaluate the responsiveness at the surface of the working electrode 4, by comparing the case where the intermediate membrane 12 intervenes between the membrane 11 and the working electrode 4, to the case where an intermediate membrane between the membrane 11 and working electrode 4 is absent Two peracetic acid concentration meters, D and E, were used during the test, each having a sensor part including: a membrane that allowed peracetic acid to permeate; an internal solution that dissolved peracetic acid having permeated the membrane; and a working electrode and a counter electrode that were immersed in the internal solution.

The sample solution, used for the test was a peracetic acid solution.

The peracetic acid concentration meter D had the above-described configuration and was equipped with the following members: a silicon membrane, porous to peracetic acid; a phosphate buffer solution; a gold working electrode, and a platinum counter electrode.

The peracetic acid concentration meter E was identical to peracetic acid concentration meter D in having the same membrane, internal solution, working electrode, and counter electrode. However, in addition to the above-described configuration of peracetic acid concentration meter D, peracetic acid concentration meter E was supplied with an intermediate membrane as well. The intermediate membrane was configured such that the working electrode contacted with the membrane via the intermediate membrane. Said intermediate membrane was formed from polycarbonate, a porous film having innumerable fine pores of a diameter of 0.05 μm to 100 μm.

The above-described peracetic acid concentration meters D and E were used to perform the following tests.

<Peracetic Acid Concentration Measurement Test>

Figure 9:
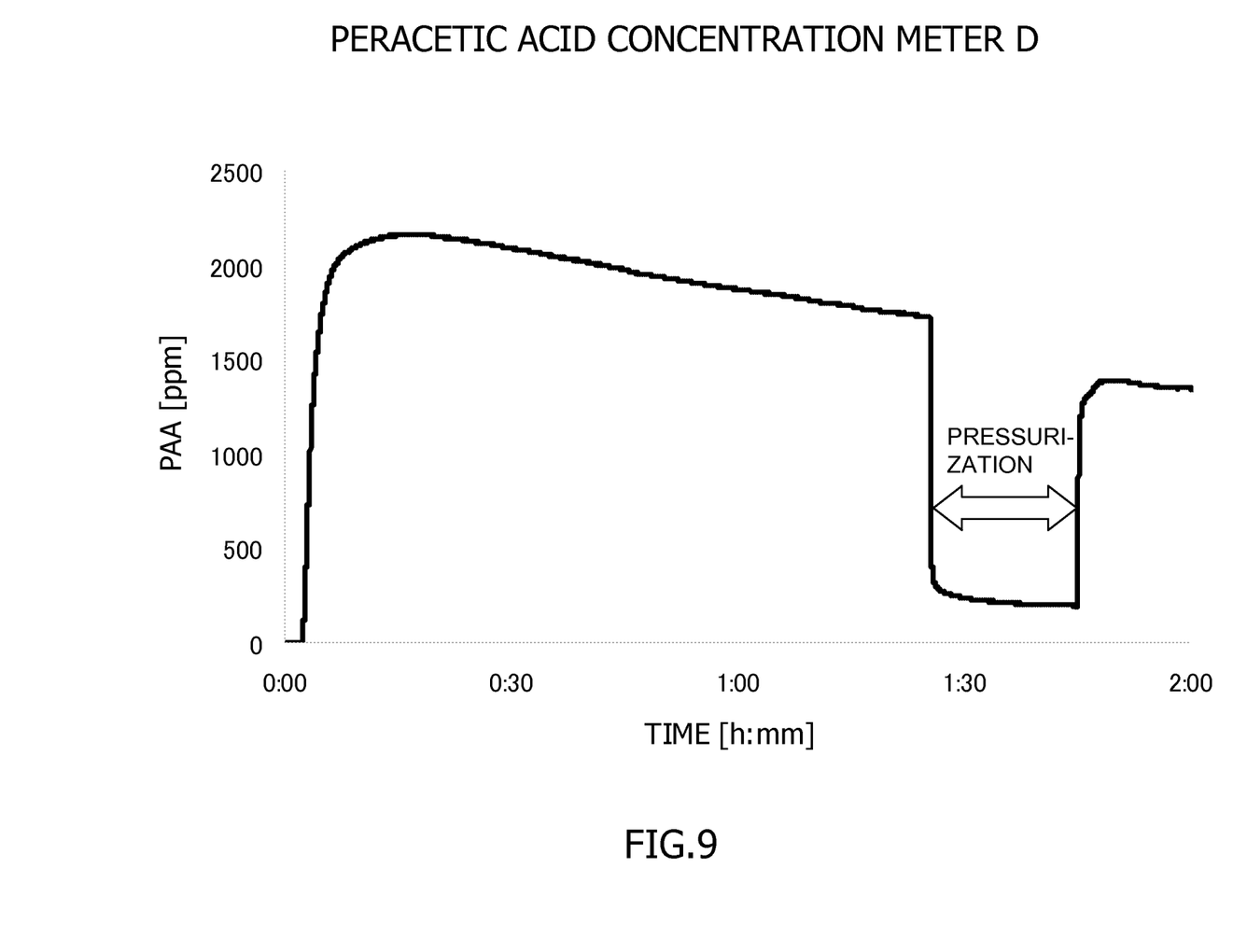
FIG. 9 is a graph illustrating a result of measuring peracetic acid concentration using a peracetic acid concentration meter D.
Figure 10:
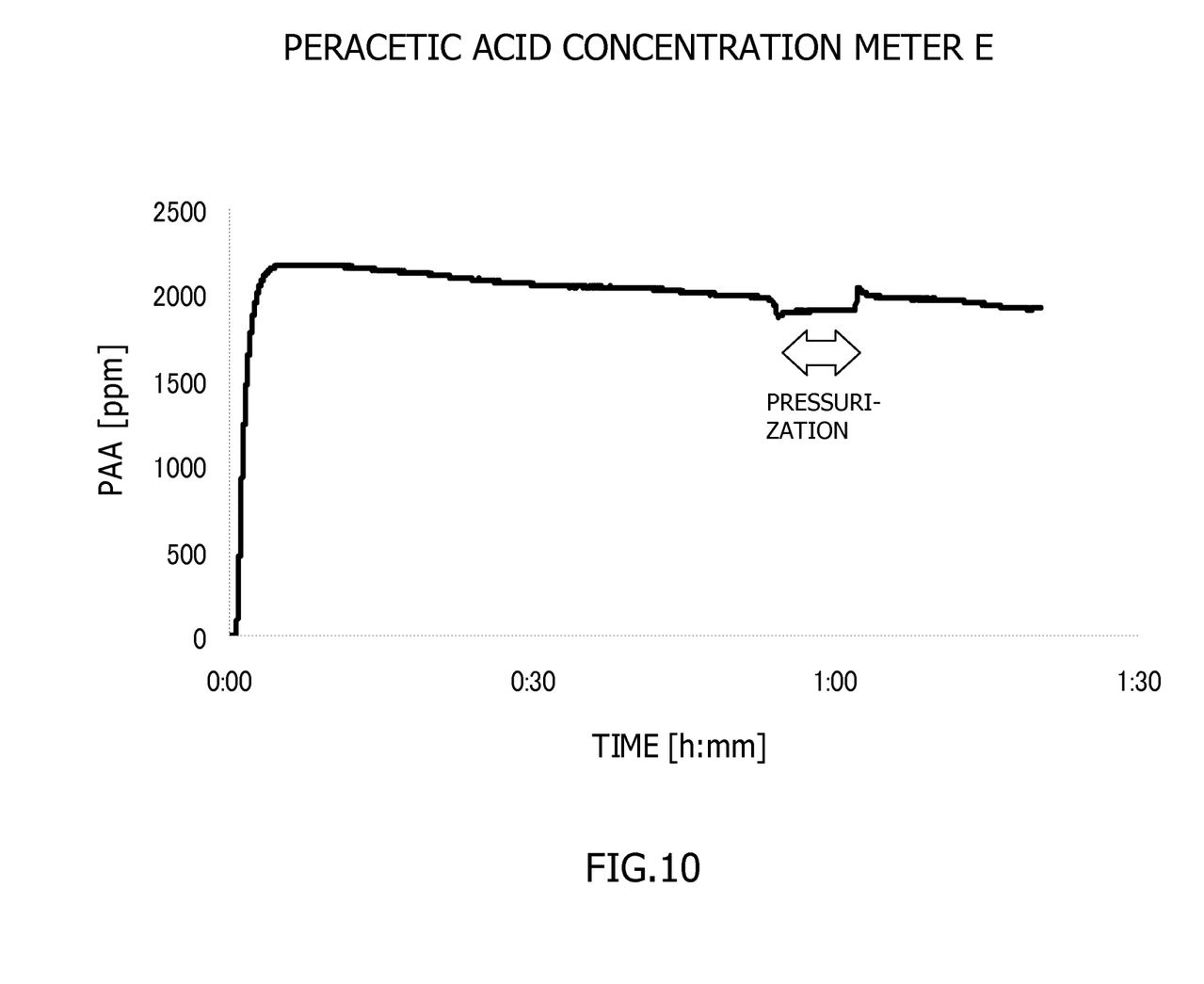
FIG. 10 is a graph illustrating a result of measuring peracetic acid concentration using a peracetic acid concentration meter E.

The above-described peracetic acid concentration meters D and E were immersed in the sample solution, and peracetic acid concentrations were calculated from current values respectively sensed by the peracetic acid concentration meters D and E. FIGS. 9 and 10 are graphs illustrating the results of the calculation. In both graphs, the vertical axis represents acetic acid concentration and the horizontal axis represents time.

<Pressure Test>

The conditions of the pressure test were as follows. The flow rate of sample solution to the working electrode was kept constant throughout the experiment. Pressure, measured in units of kPa was applied to the membrane, forcing the membrane to press against the working electrode. The pressure applied to the membrane started at 0 kPa, was raised up to 100 kPa, and was finally brought down to 0 kPa again.

FIG. 9 illustrates the test results in the case of using the peracetic acid concentration meter D. As illustrated in FIG. 9, the peracetic acid concentration meter D stably measured the peracetic acid concentration before any pressure was applied.

However, after pressure was applied, the peracetic acid concentration value measured by the peracetic acid concentration meter D drastically decreased. Finally, after pressure was decreased again to the no-applied-pressure state of the beginning of the test, the peracetic acid concentration value drastically increased, and the peracetic acid concentration meter D stably measured the peracetic acid concentration as it did before pressure was applied.

Next, FIG. 10 illustrates the test results in the case of using the peracetic acid concentration meter E. As illustrated in FIG. 10, the peracetic acid concentration meter E stably measured the peracetic acid concentration throughout the duration of the test, and did not show any sign of the measurement being affected by a change in pressure.

From the above results, it can be deducted that the peracetic acid concentration meter D which did not have an intermediate membrane, could not reliably measure peracetic acid when pressure was applied to the membrane. Whereas tin the case of using peracetic acid concentration meter E, peracetic acid concentration could be measured stably regardless of the change in pressure applied to the membrane.

The reason for the different results for peracetic concentration meters D and E may be attributed to the presence or absence of an intermediate membrane. In the absence of a membrane, as was the case in peracetic acid concentration meter D, when applying pressure to the membrane, the membrane and the working electrode come in direct contact with each other and forced against each other tightly, reducing the effective area on the surface of the working electrode where the internal solution can be supplied for an oxidation-reduction reaction to take place. Consequently, the reaction at the surface of the working electrode is blocked, and the responsiveness of the working electrode deteriorates.

On the other hand, in the case where an intermediate membrane that is porous and has wettability with respect to fluid, is present in between the membrane 11 and the working electrode 4, as was the case in peracetic concentration meter E, even when applying pressure to the membrane, peracetic acid dissolved in the internal solution can be stably be supplied to the surface of the working electrode from the liquid layers of the internal solution provided on the surfaces of the intermediate membrane and through the innumerable fine pores provided in the intermediate membrane, and therefore the peracetic acid concentration can be stably measured.

Further, when comparing FIGS. 9 and 10, it turns it is evident that the rise of the graph in FIG. 10 is obviously quicker than the rise of the graph in FIG. 9. This implies that the responsiveness of the sensor part of the peracetic acid concentration meter E is quicker and more sensitive than that of the peracetic acid concentration meter D.

The reason for this difference may also be attributed to the presence or absence of an intermediate membrane in between the membrane and the working electrode. In the case of the peracetic acid concentration meter D, which did not include an intermediate membrane in between the working electrode and the membrane, the working electrode and the membrane were likely forced in to close contact with each other, making it difficult to supply the internal solution to the surface of the working electrode, due to a reduction in the effective surface area of the working electrode. Whereas, in the case of the peracetic acid concentration meter E, where an intermediate membrane was present between the working electrode and the membrane, the intermediate membrane ensured that a steady supply of internal solution was present at the surface of the working electrode throughout the test, and that a reaction could stably take place.

For this reason, by proving an intermediate membrane 12 in between the working electrode 4 and the membrane 11, the responsiveness of the sensor part 1 can be improved, and also the sensor part 1 can be made more stable.

In addition, by forming the intermediate membrane 12 from a polymer or similar material, particularly a polycarbonate, the responsiveness of the working electrode 4 can be further improved.

TABLE 1

| Intermediate membrane | Pore diameter | Film thickness | 90% response time |
|---|---|---|---|
| Polycarbonate | 0.1 µm-10 µm | 7 µm | 3 to 5 min. |
| PTFE | 0.01 µm-5.0 µm | 150-200 µm | 12 to 13 min. |
| PP + PE | 0.01 µm-3.0 µm | 10-100 µm | 22 min. or more |
| Polyimide | 30-100 µm | 20-60 µm | 7 to 12 min. |

Table 1 shown above lists 90% response times in the case of using the respective materials for the intermediate membrane.

As listed in Table 1, it turns out that polycarbonate exhibits a quick 90% response time as compared to the 90% response time of alternative materials. The reason for this may be that the film thickness of the polycarbonate is relatively thin in comparison with the other materials. The thickness of polycarbonate makes it possible to shorten the time required for the internal solution to permeate the polycarbonate film, and therefore as compared with the other materials, the response time can be made quicker, which helps to improve the responsiveness of the sensor.

On the other hand, it turns out that the mixed resin (PP+PE) using polypropylene and polyethylene exhibits a slow 90% response time when compared with the alternative materials. The reason for this may be that in addition to having a small pore diameter, the fine pores of mixed resin are randomly arranged relative to the fine pores of polycarbonate, PTFE, and polyimide, which are relatively orderly arrayed. Therefore the time required for the internal solution to permeate the mixed resin is larger than the required for the other materials.

These results indicate that in order to improve responsiveness of the sensor, it is necessary to decrease the thickness of the intermediate membrane, to increase the pore diameter of fine pores of the intermediate membrane to the extent of preventing intrusion of air bubbles, and to provide an intermediate membrane with orderly arrayed pores.

However, it is important to note that if the thickness of the intermediate membrane is made too thin, the intermediate membrane may be damaged. Accordingly, the thickness of the intermediate membrane is desirably 1 µm to 100 µm. Also, the pore diameter of the fine pores is desirably 0.05 µm to 100 µm depending on the material used and the thickness of the intermediate membrane.

It is worth noting that the above-described results also suggest the responsiveness of the sensor can be improved by forming the membrane 11 with a relatively thin thickness.

The present invention is not limited to the above-described embodiment.

In the above-described embodiment, the internal solution consists of only the buffer solution. However, the internal solution may be one consisting of a buffer solution and a material unreactive with peracetic acid. For example, as a material unreactive with peracetic acid, a material also unreactive with a biological material can be used as well. In such a case, even if the internal solution leaks toward the sample solution side, in such a configuration a reaction between the internal solution and the buffer solution will be prevented, and the disinfecting/sterilizing effect of the sample solution will be maintained.

In addition, as long as the material contained in the internal solution is unreactive with a biological material, even in the event that the internal solution leaks in to the sample solution side, there will be no contamination or adverse effect on living bodies in the sample solution.

Finally, the above-described peracetic acid concentration meter can also be applied to a membrane covered type sensor. Such a membrane covered type sensor could be used to sense a specific substance contained in a sample solution, such as peracetic acid, hydrogen peroxide, dissolved oxygen, or residual chlorine.

The present invention can be modified in various ways without departing from the scope thereof. And technical features described in the above embodiments can also be combined.

REFERENCE SIGNS LIST

4: Working electrode
5: Counter electrode
11: Membrane
13: Internal solution
15: Protective film

The invention claimed is:

1. A membrane covered type peracetic acid concentration meter that measures concentration of peracetic acid in a sample solution, the peracetic acid concentration meter comprising:
   a membrane that allows peracetic acid to permeate;
   an internal solution that dissolves peracetic acid having permeated the membrane;
   a working electrode and a counter electrode that are immersed in the internal solution, such that an oxidation-reduction reaction of the permeated peracetic acid continuously occurs at surfaces of the working electrode to maintain a constant electric current through the electrodes for a predetermined time duration, thereby allowing the concentration meter to accurately measure the concentration of peracetic acid in the sample solution; and
   a protective material provided on a surface of the membrane on a sample solution side except in a region proximate the working electrode, the protective material being impermeable to liquid, wherein
   the working electrode is in contact with the membrane via an intermediate membrane having wettability with respect to the internal solution.

2. The peracetic acid concentration meter according to claim 1, wherein
   the internal solution contains materials unreactive with peracetic acid.

3. The peracetic acid concentration meter according to claim 1, wherein
   the membrane is made from a material containing silicon, fluororesin, or polyethylene.

4. A method of measuring peracetic acid concentration by using the peracetic acid concentration meter according to claim 1, the method comprising:
   providing the membrane that allows peracetic acid to permeate;
   providing the working electrode in contact with the membrane via the intermediate membrane; and
   dissolving peracetic acid that has permeated the membrane with the internal solution that dissolves peracetic acid.

5. A membrane covered type peracetic acid concentration meter that measures concentration of peracetic acid in a sample solution, the peracetic acid concentration meter comprising:
   a membrane that allows peracetic acid to permeate;
   an internal solution that dissolves peracetic acid having permeated the membrane;
   a working electrode and a counter electrode that are immersed in the internal solution, such that an oxidation-reduction reaction of the permeated peracetic acid continuously occurs at surfaces of the working electrode to maintain a constant electric current through the electrodes for a predetermined time duration, thereby allowing the concentration meter to accurately measure the concentration of peracetic acid in the sample solution; and
   a protective material provided on a surface of the membrane on a sample solution side except in a region proximate the working electrode, the protective material being impermeable to liquid, wherein
   a buffer solution having a buffering effect on hydrogen ion concentration is the internal solution, and
   the working electrode is in contact with the membrane via an intermediate membrane having wettability with respect to the internal solution.

6. The peracetic acid concentration meter according to claim 5, wherein
   the intermediate membrane is a porous membrane.

7. The peracetic acid concentration meter according to claim 5, wherein
   the intermediate membrane is made from a polymer.

8. The peracetic acid concentration meter according to claim 1, wherein
   the protective material is a protective film.

* * * * *